United States Patent [19]

Maehr

[11] Patent Number: 5,523,310
[45] Date of Patent: Jun. 4, 1996

[54] 1,2,3-TRIAZOLE DERIVATIVES

[75] Inventor: Hubert Maehr, Wayne, N.J.

[73] Assignee: Hoffmann-La Roche Inc., Nutley, N.J.

[21] Appl. No.: 349,225

[22] Filed: Dec. 5, 1994

[51] Int. Cl.$^6$ .................. A61K 31/41; C07D 249/04
[52] U.S. Cl. .......................... 514/359; 548/255
[58] Field of Search .................. 548/255; 514/359

[56] References Cited

U.S. PATENT DOCUMENTS 4,908,363  3/1990  Klötzer et al. ............. 514/235.8
5,189,048  2/1993  Carini et al. ............... 514/359

OTHER PUBLICATIONS

Chem. Ber. vol. 106, pp. 2758–2766 (1973), Beck, G.
Int. J. Immunopharma, 12: pp. 703–712 (1990), Hanglow, A. C.
Amer. J. Clin. Path. 35: pp. 223–232 (1961) Goodwin, J. F.
Anal. Biochem. 86: pp. 248–254 (1976) Bradford, M. M.

Primary Examiner—Jacqueline Haley
Attorney, Agent, or Firm—George M. Gould; George W. Johnston; Robert A. Silverman

[57] ABSTRACT

The invention relates to a compound of the formula

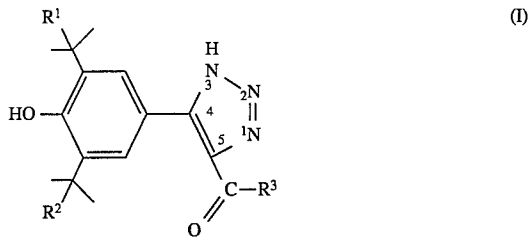

wherein the substituents are as defined herein; its tautomer wherein the hydrogen of the triazole ring occupies position 1 of the triazole ring, and a pharmaceutically acceptable salt of the compound of formula I wherein $R^3$ is —OH or its tautomer wherein the hydrogen of the triazole ring occupies position 1 of the triazole ring. The compounds of formula I and their salts possess inflammation inhibiting properties and are therefore useful in the treatment of inflammations such as inflammatory joint disease, for example, arthritis. In another aspect, the invention relates to pharmaceutical compositions and methods of use comprising the compounds of formula I.

15 Claims, No Drawings

1,2,3-TRIAZOLE DERIVATIVES

BRIEF SUMMARY OF THE INVENTION

The invention relates to a compound of the formula

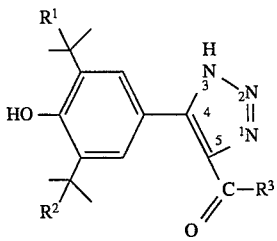

(I)

wherein $R^1$ and $R^2$ are independently lower alkyl;

$R^3$ is —$NR^4R^5$ or —$OR^6$;

$R^4$ is hydrogen, lower alkyl, lower alkenyl, lower alkoxy, cyclopropyl, fluoro substituted lower alkyl, chloro substituted lower alkyl, hydroxy substituted lower alkyl, alkoxy substituted lower alkyl, or amino substituted lower alkyl;

$R^5$ is hydrogen, hydroxy, alkyl, alkenyl, alkoxy, cycloalkyl, fluorosubstituted alkyl, chloro substituted alkyl, hydroxy substituted alkyl, alkoxy substituted alkyl, amino substituted alkyl, phenyl, phenoxy, phenyl substituted alkyl, phenyl substituted alkenyl, phenoxy substituted alkyl, phenylcarbonyl, alkylcarbonyl, or a 5 or 6 membered heterocyclic group;

when $R^4$ is hydroxy or lower alkoxy, $R^5$ is not hydroxy, alkoxy or phenoxy; and $R^6$ is hydrogen, alkyl, phenyl or phenyl substituted alkyl; its tautomer wherein the hydrogen of the triazole ring occupies position 1 of the triazole ring, and a pharmaceutically acceptable salt of the compound of formula I wherein $R^3$ is —OH or its tautomer wherein the hydrogen of the triazole ring occupies position 1 of the triazole ring.

The compounds of formula I and their tautomers and salts described above possess inflammation inhibiting properties and are therefore useful in the treatment and prevention of inflammations such as inflammatory joint disease, for example, arthritis.

In another aspect, the invention relates to pharmaceutical compositions comprising an inert carrier and a compound of formula I, its tautomer or its salt described above. In another aspect, the invention relates to methods of using the compounds of formula I, and their tautomers and salts described above, for the treatment or prevention of inflammations such as inflammatory joint disease, for example, arthritis.

In yet another aspect, the invention relates to a process for preparing a compound of the formula

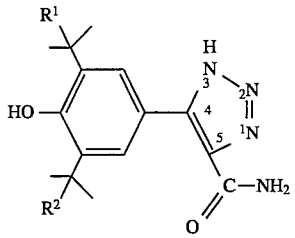

(Ia)

and its tautomer described above wherein the hydrogen of the triazole ring occupies position 1 of the triazole ring. The method comprises reacting a compound of the formula

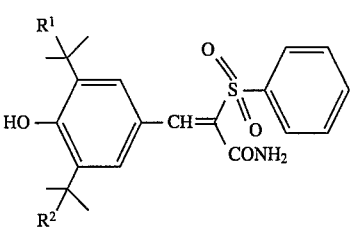

(II)

with sodium azide to yield a compound of formula Ia or its tautomer described above.

In yet another aspect, the invention relates to a compound of the formula

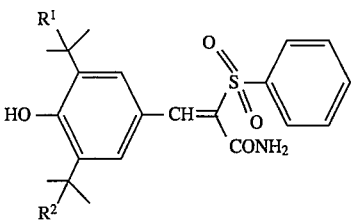

(II)

In yet another aspect, the invention relates to a process for preparing a compound of the formula

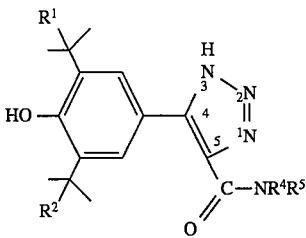

(Ib)

and its tautomer wherein the hydrogen of the triazole ring occupies position 1 of the triazole ring. The method comprises reacting the compound of the formula

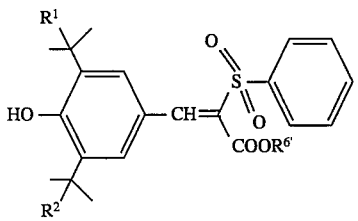

(III)

wherein $R^{6'}$ is alkyl, phenyl or phenyl substituted alkyl with sodium azide to yield a compound of the formula

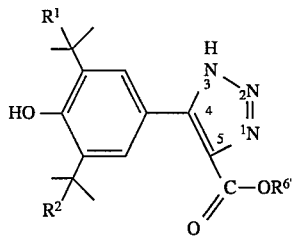

(Ic)

or its tautomer wherein the hydrogen of the triazole ring occupies position 1 of the triazole ring. The compound thus prepared is converted to a compound of the formula Ib or the above described tautomer thereof by aminolysis using the appropriate amine compound of the formula $HNR^4R^5$. Preferably, conversion of the compound of formula Ic or its tautomer described above to a compound of formula Ib or its tautomer described above comprises hydrolyzing the compound of formula Ic or its tautomer to a compound of formula

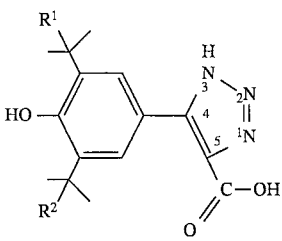

(Id)

or its tautomer wherein the hydrogen of the triazole ring occupies position 1 of the triazole ring and then reacting the compound of formula Id or its tautomer described above with a compound of formula NHR⁴R⁵ to yield a compound of formula Ib or its tautomer described above.

In yet another aspect, the invention relates to a compound of the formula

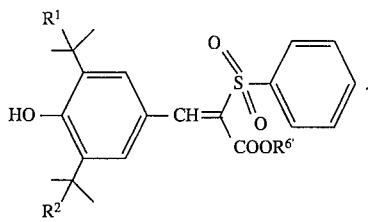

(III)

In yet another aspect, the invention relates to a compound of the formula

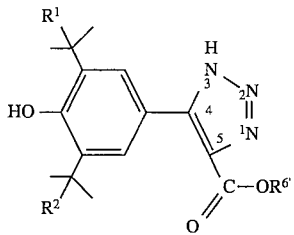

(Ic)

or its tautomer wherein the hydrogen of the triazole ring occupies position 1 of the triazole ring.

In yet another aspect, the invention relates to a compound of the formula

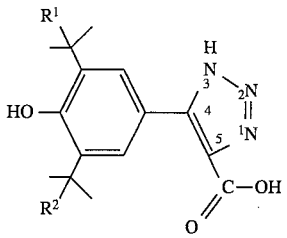

(Id)

or its tautomer wherein the hydrogen of the triazole ring occupies position 1 of the triazole ring.

DETAILED DESCRIPTION OF THE INVENTION

The invention relates to a compound of the formula

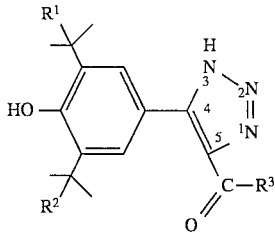

(I)

wherein $R^1$ and $R^2$ are independently lower alkyl;

$R^3$ is —$NR^4R^5$ or —$OR^6$;

$R^4$ is hydrogen, hydroxy, lower alkyl, lower alkenyl, lower alkoxy, cyclopropyl, fluoro substituted lower alkyl, chloro substituted lower alkyl, hydroxy substituted lower alkyl, alkoxy substituted lower alkyl, or amino substituted lower alkyl;

$R^5$ is hydrogen, hydroxy, alkyl, alkenyl, alkoxy, cycloalkyl, fluoro substituted alkyl, chloro substituted alkyl, hydroxy substituted alkyl, alkoxy substituted alkyl, amino substituted alkyl, phenyl, phenoxy, phenyl substituted alkyl, phenyl substituted alkenyl, phenoxy substituted alkyl, phenylcarbonyl, alkylcarbonyl, or a 5 or 6 membered heterocyclic group;

when $R^4$ is hydroxy or lower alkoxy, $R^5$ is not hydroxy, alkoxy or phenoxy; and $R^6$ is hydrogen, alkyl, phenyl, or phenyl substituted alkyl;

its tautomer wherein the hydrogen of the triazole ring occupies position 1 of the triazole ring, and a pharmaceutically acceptable salt of the compound of formula I wherein $R^3$ is —OH or its tautomer wherein the hydrogen of the triazole ring occupies position 1 of the triazole ring.

As used herein, the term "alkyl" denotes a $C_1$–$C_{12}$ straight, saturated hydrocarbon chain, including but not limited to methyl, ethyl, n-propyl, n-butyl, and the like. The term "lower alkyl" denotes a $C_1$–$C_4$ alkyl.

The term "alkenyl" denotes a $C_2$–$C_{12}$ straight, unsaturated hydrocarbon chain, including but not limited to ethenyl, 1-propenyl, 2-propenyl, 1-butenyl, 2-butenyl, and the like. The term "lower alkenyl" denotes a $C_2$–$C_4$ alkenyl.

The term "alkoxy" denotes a $C_1$–$C_{12}$ straight chain alkoxy residue, including but not limited to methoxy, ethoxy, n-butoxy, and the like. The term "lower alkoxy" denotes a $C_1$–$C_4$ alkoxy.

The term "cycloalkyl" denotes a $C_3$–$C_6$ saturated, cyclic hydrocarbon residue, including cyclopropyl, cyclobutyl, cyclopentyl and cyclohexyl.

The term "fluoro substituted alkyl" denotes a $C_1$–$C_{12}$ straight chain saturated hydrocarbon radical substituted with one or more fluorine atoms, including, but not limited to, 2-fluoroethyl, 2,2,2-trifluoroethyl, and the like.

The term "chloro substituted alkyl" denotes a $C_2$–$C_{12}$ straight chain saturated hydrocarbon radical substituted with one or more chlorine atoms, including, but not limited to, 2-chloroethyl, 2,2,2-trichloroethyl and the like.

The term "hydroxy substituted alkyl" denotes a $C_1$–$C_{12}$ straight chain saturated hydrocarbon radical substituted with one or more hydroxy groups, including, but not limited to, 1-hydroxymethyl, 1-hydroxyethyl, and the like.

The term "alkoxy substituted alkyl" denotes a $C_1$–$C_{12}$ straight chain saturated hydrocarbon radical substituted with one or more $C_1$–$C_{12}$ straight chain alkoxy residues.

The term "amino substituted alkyl" denotes a $C_1$–$C_{12}$ straight chain saturated hydrocarbon moeity substituted with one or more amino groups in which one or both hydrogens may be replaced by hydroxy, alkyl, alkenyl, alkoxy, cycloalkyl, fluoro substituted alkyl, hydroxy substituted alkyl, alkoxy substituted alkyl, phenyl substituted alkyl, phenyl substituted alkenyl, phenoxy substituted alkyl, phenylcarbonyl, alkylcarbonyl, or a 5 or 6 membered heterocyclic group, for example, 2-(dimethylamino)ethyl.

The term "phenyl" denotes an unsubstituted or substituted phenyl group wherein the substituents are chosen from halogen, cyano, nitro, halosubstituted alkyl, aminosulfonyl, alkylaminosulfonyl and acetamido.

The term "phenoxy" denotes a phenoxy residue in which the phenyl group is unsubstituted or substituted phenyl group wherein the substituents are chosen from halogen, cyano, nitro, halosubstituted alkyl, aminosulfonyl, alkylaminosulfonyl and acetamido.

The term "phenyl substituted alkyl" denotes a $C_1$–$C_{12}$ straight, saturated hydrocarbon chain substituted by an unsubstituted or substituted phenyl group wherein the substituents of the phenyl group are chosen from halogen, cyano, nitro, halosubstituted alkyl, aminosulfonyl, alkylaminosulfonyl and acetamido, including but not limited to benzyl, 1-phenethyl, 2-phenethyl, and the like.

The term "phenyl substituted alkenyl" denotes a $C_2$–$C_{12}$ straight, unsaturated hydrocarbon chain substituted by an unsubstituted or substituted phenyl group wherein the substituents of the phenyl group are chosen from halogen, cyano, nitro, halosubstituted alkyl, aminosulfonyl, alkylaminosulfonyl and acetamido, including but not limited to phenylethenyl, 3-phenyl-2-propenyl, and the like.

The term "phenoxy substituted alkyl" denotes a $C_1$–$C_{12}$ straight, saturated hydrocarbon chain substituted by a phenoxy residue in which the phenyl group is unsubstituted or substituted phenyl group wherein the substituents are chosen from halogen, cyano, nitro, halosubstituted alkyl, aminosulfonyl, alkylaminosulfonyl and acetamido, including but not limited to benzyloxy and the like.

The term "phenyl carbonyl" denotes a carbonyl group substituted by an unsubstituted or substituted phenyl group wherein the substituents of the phenyl group are chosen from halogen, cyano, nitro, halosubstituted alkyl, aminosulfonyl, alkylaminosulfonyl and acetamido, including but not limited to benzoyl and the like.

The term "alkylcarbonyl" denotes a carbonyl group substituted by a $C_1$–$C_{12}$ straight, saturated hydrocarbon chain.

The term "5 or 6 membered heterocyclic" denotes a 5 or 6 membered cyclic hydrocarbon in which one or more of the ring carbon atoms is replaced, independently, by oxygen, nitrogen, or sulfur, including but not limited to imidazolyl, thiophenyl, furyl, pyridinyl, pyrimidinyl, and the like.

In formula I, conveniently $R^1$ and $R^2$ can each be methyl.

Preferred are compounds wherein $R^3$ is —$NR^4R^5$.

When $R^3$ is —$NR^4R^5$, it is preferred that $R^4$ is hydrogen, methyl, methoxy, ethyl, or ethoxy, most preferably hydrogen.

When $R^3$ is —$NR^4R^5$, it is preferred that $R^5$ is hydrogen, hydroxy, $C_1$–$C_7$ alkyl, $C_2$–$C_7$ alkenyl, $C_1$–$C_7$ alkoxy, cyclopropyl, fluorosubstituted $C_1$–$C_7$ alkyl or hydroxysubstituted $C_1$–$C_7$ alkyl, most preferably hydrogen, hydroxy, methyl, ethyl, methoxy, cyclopropyl, 2-fluoroethyl, 2,2,2-trifluoroethyl or 2-hydroxyethyl.

Especially preferred compounds of formula I are:

4-[3,5-bis(1,1-dimethylethyl)-4-hydroxyphenyl]-1(or3)H-1,2,3-triazole-5-carboxamide;

4-[3,5-bis(1,1-dimethylethyl)-4-hydroxyphenyl]-N-methyl-1(or3)H-1,2,3-triazole- 5-carboxamide;

4-[3,5-bis(1,1-dimethylethyl)-4-hydroxyphenyl]-N-ethyl-1(or3)H-1,2,3-triazole- 5-carboxamide;

4-[3,5-bis(1,1-dimethylethyl)-4-hydroxyphenyl]-N-methoxy-1(or3) H-1,2,3-triazole- 5-carboxamide ;

4-[3,5-bis(1,1-dimethylethyl)-4-hydroxyphenyl]-N-hydroxy-N-methyl-1(or3)H-1,2,3-triazole-5-carboxamide;

4-[3,5-bis(1,1-dimethylethyl)-4-hydroxyphenyl]-N-(cyclopropyl)-1(or3 )H-1,2,3-triazole-5-carboxamide;

4-[3,5-bis(1,1-dimethylethyl)-4-hydroxyphenyl]-N-(2,2,2trifluoroethyl)-1(or3)H-1,2,3-triazole-5-carboxamide;

4-[3,5-bis(1,1-dimethylethyl)-4-hydroxyphenyl]-N-(2-fluoroethyl)-1(or3)H-1,2,3-triazole-5-carboxamide; and 4-[3,5-bis(1,1-dimethylethyl)-4-hydroxyphenyl]-N-(2hydroxyethyl)- 1 (or3)H-1,2,3-triazole-5-carboxamide.

The compounds of formula I wherein $R^3$ is —$NH_2$ and its tautomer described above can be prepared in accordance with Reaction Scheme I. In Reaction Scheme 1, $R^1$ and $R^2$ are as described above.

REACTION SCHEME I

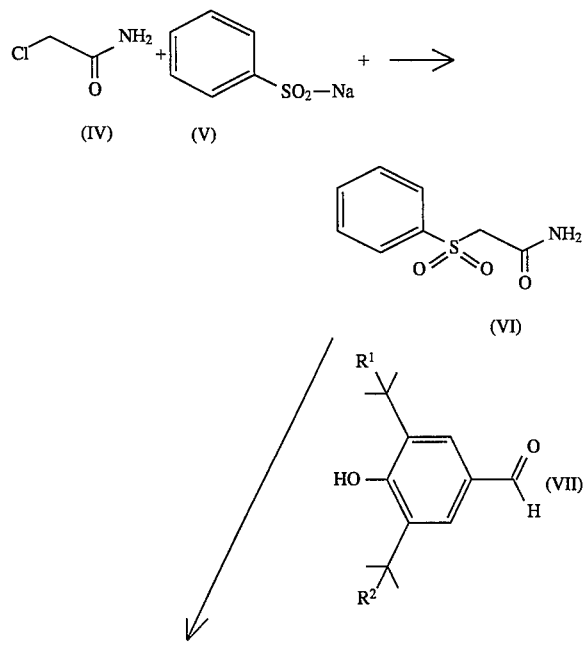

REACTION SCHEME I
-continued

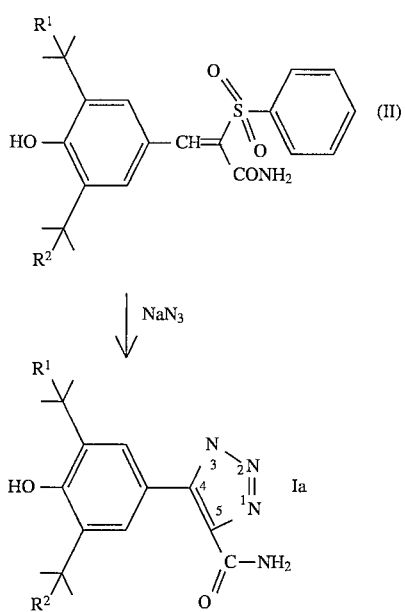

REACTION SCHEME II

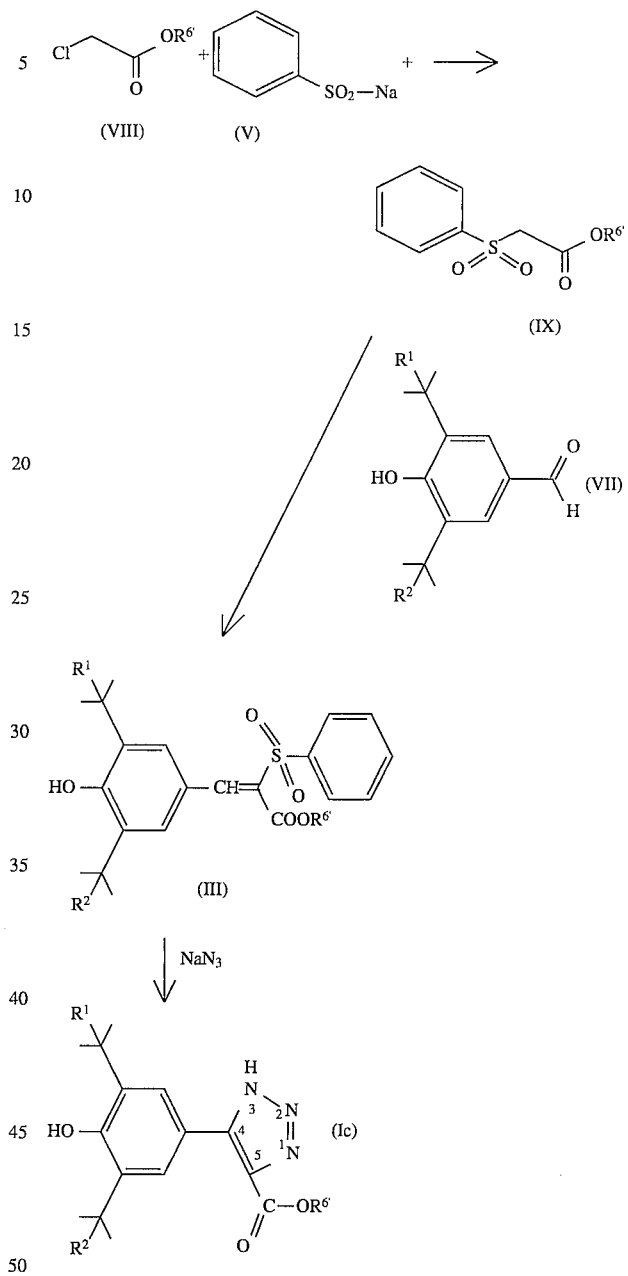

In Reaction Scheme I, the starting materials of formulas IV, V and VII are known or can be prepared readily according to methods which are known and which are familiar to a person skilled in the art.

A compound of formula IV, which is a known compound, is condensed by conventional methods with a compound of formula V, which is a known compound, in the presence of a polar, nonprotic solvent such as dimethylsulfoxide at from about 80° C. to about 120° C. A resulting compound of formula VI is recovered, for example by precipitation upon addition of water, and then purified, for example by recrystallization. The compound of formula VI is condensed with a compound of formula VII, which is a known compound, for example 4-hydroxy-3,5-di-t-butylbenzaldehyde, or which can be prepared by known procedures. The condensation is under conventional Knoevenagel condensation reaction conditions for a period of from about 36 to about 48 hours, preferably using as a solvent a mixture of toluene and cyclohexane (instead of benzene), N,N-dimethylformamide, and 1-methylpiperazine. Crystallization of a resulting compound of formula II is completed by addition of hexane. The compound of formula II is reacted with sodium azide in the presence of an organic solvent under conditions described in *Chem Ber.*, vol. 106, p. 2758 (1973) except that methoxyethanol is used as the organic solvent rather than N,N-dimethylformamide. A resulting compound of formula Ia or its tautomer described above is recovered, for example by precipitation upon addition of water, and then purified, for example by recrystallization. Compounds of formula I wherein $R^3$ is $-OR^{6'}$ and its tautomers described above can be prepared in accordance with Reaction Scheme II. In Reaction Scheme II, $R^1$, $R^2$ and $R^{6'}$ are as described above.

In Reaction Scheme II, the starting material of formula VIII is a known compound, such as methylchloroacetate and ethyl chloroacetate, or can be prepared according to known procedures, for example reacting chloroacetyl chloride with a compound of the formula $R^{6'}OH$.

A compound of formula VIII is condensed with a compound of formula V under conditions described in Reaction Scheme 1 for the reaction of a compound of formula IV and a compound of formula V. A resulting compound of formula IX is recovered, for example by precipitation upon additon of water, and then purified, for example by recrystallization or distillation. The compound of formula IX is condensed with a compound of formula VII, conveniently 4-hydroxy-3,5-di-t-butylbenzaldehyde, under conventional Knoevenagel condensation reaction conditions, preferably using as a solvent a mixture of toluene and cyclohexane (instead of benzene) and 1-methylpiperazine. Crystallization of the resulting compound of formula III is completed by the addition of hexane. The compound of formula III is reacted with sodium azide under conditions described in Reaction Scheme 1 for the reaction of a compound of formula II with sodium azide. A resulting compound of formula Ic or its tautomer described above is recovered, for example by precipitation upon additon of water, and then purified, for example by recrystallization.

Compounds of formula I wherein $R^3$ is OH and their tautomers described above can be prepared in accordance with Reaction Scheme III. In Reaction Scheme III, $R^1$, $R^2$ and $R^{6'}$ are as described above.

REACTION SCHEME III

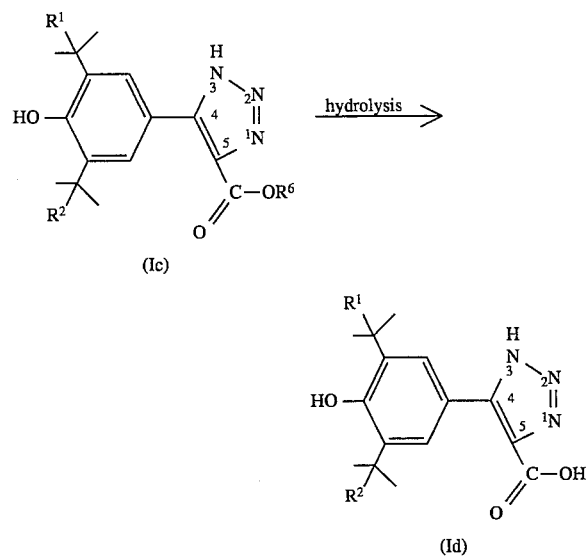

In Reaction Scheme III, a compound of formula Id or its tautomer described above is prepared by hydrolysis of a compound of formula Ic or its tautomer described above, which can be prepared according to procedures described above in Reaction Scheme II. The hydrolysis is carried out under conventional saponification conditions using 1 equivalent of a suitable inorganic hydroxide such as sodium hydroxide. Upon acidification an aqueous suspension of the acid results. A resulting compound of formula Id or its tautomer described above is recovered, for example by precipitation upon addition of water, and then purified, for example by recrystallization.

Compounds of formula I wherein $R^3$ is —$NR^4R^5$ and its tautomers described above can be prepared in accordance with Reaction Scheme IV. In Reaction Scheme IV, $R^1$, $R^2$, $R^4$ and $R^5$ are as described above.

REACTION SCHEME IV

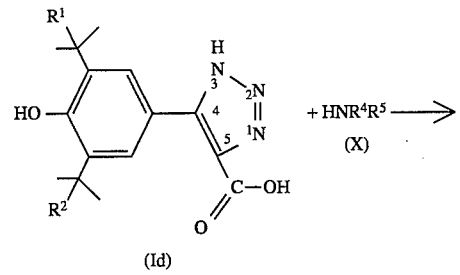

-continued
REACTION SCHEME IV

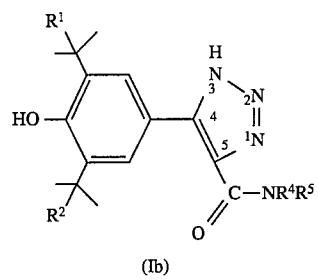

In Reaction Scheme IV, a compound of formula Ib or its tautomer described above is prepared by condensing a compound of formula Id or its tautomer described above, which can be prepared according to procedures described above in Reaction Scheme III, with a compound of formula $HNR^4R^5$. The condensation is under conventional peptide synthesis condensation, preferably using an activating agent for the carboxyl group, such as benzotriazol-1-yloxytris-(dimethylamino)phosphonioum hexafluorophosphate, 1 equivalent of a compound of the formula $NHR^4R^5$, and 1 equivalent of a tertiary amine such as N,N-diisopropylethylamine. If the compound of the formula $NHR^4R^5$ exists only as a salt, then 2 equivalents of the tertiary amine is used. A resulting compound of formula Ib or its tautomer described above is recovered, for example upon addition of water, and then purified, for example by recrystallization.

The invention also relates to pharmaceutically acceptable salts of the compounds of formula I wherein $R^3$ is —OH and tautomers thereof described above. A compound of formula I wherein $R^3$ is —OH and its tautomers can be converted into a corresponding salt by reaction with any basic compound which has a non-toxic, pharmacologically acceptable cation. Suitable bases thus include, for example, alkali metal hydroxides and carbonates such as potassiom carbonate and the like; alkaline earth metal hydroxides and carbonates, for example, calcium carbonate; quaternary amines such as choline; and the like. One skilled in the art will appreciate that the variety of salts embraced by the invention is limited only by the criterion that a base employed in forming the corresponding salts be both non-toxic and physiologically acceptable.

As mentioned earlier, the compounds of formula I, their tautomers described above, and pharmaceutically acceptable salts of compounds of formula I wherein $R^3$ is OH and their tautomers described above are useful in the treatment or prevention of inflammations. For example, they can be used as anti-inflammatory agents in the treatment of inflammatory joint diseases, such as arthritis.

Representative compounds of formula I and their tautomers described above were tested for their inflammation-inhibiting properties in an adjuvent-induced arthritis test described in Int. J. Immunopharma., 12: 709–712 (1990).

0.1 ml of a 0.5% (weight/volume) suspension of heat-killed and dried Mycobacterium butyricum in heavy mineral oil, containing 0.2% digitionin, is injected into the base of the tail of male Lewis rats (120–140 g). The animals are housed individually and receive feed and water ad libitum. The thus-induced arthritis is allowed to develop without treatment during 21 days. On day 21 the body weight of each animal is determined. At the same time, the volumes of the two hind paws of each animal is measured by immersing the paws in an aqueous plethysmograph up to the height of the lateral malleolus. Thereupon, the animals are divided into groups, each group comprising six animals of approximately the same average volumes of the hind paws. One group is administered vehicle (Tween 80). The other groups are administered the test compound suspended in an aqueous suspending vehicle [0.9% NaCl (w/v) containing 0.5% carboxymethyl cellulose (w/v), 0.86% benzyl alcohol (v/v) and 0.39% Tween 80 (v/v)]. The test compound in aqueous suspending vehicle (or vehicle alone) is administered to the animals by intubation each day over a period of seven days. At the end of the treatment period (day 28), body weight and volumes of the hind paws are again determined. The changes over the treatment period is calculated. The change in paw volume or body weight equals the paw volume or body weight on day 28 minus paw volume or body weight on day 21. Subsequently, the animals are sacrificed and plasma samples are removed in order to determine the fibrinogen levels after precipitation of the removed plasma samples with sodium sulfite. Fibrinogen is determined in accordance with a modification of the method described in Amer. J. Clin. Path. 35, 227–232, 1961. The modification was the use a protein assay kit (Bio-Rad Laboratories, Inc., Hercules, Calif.) described in Biochem., 86:248 (1976) to measure fibrinogen levels.

The results determined for representative compounds of formula I in the test described hereinbefore are set forth in the following Table I. In Table I, the results for vehicle is in parenthesis following the results for each tested compound at each dose in each test.

TABLE 1

| Compound | Dosage (mg/kg) | Inflammation-Inhibiting Activity | | |
|---|---|---|---|---|
| | | Paw Volume Change (ml) | Plasma Fibrinogen (mg/ml) | Body Weight Change (g) |
| A | 3 | 0.35 ± 0.11 (1.10) | 844 ± 64 (993) | 8 ± 4 (6) |
| | 10 | −0.18 ± 0.07 (1.10) | 885 ± 35 (993) | 18 ± 1 (6) |
| | 30 | −0.54 ± 0.13 (1.03) | 817 ± 34 (1115) | 36 ± 3 (12) |
| B | 30 | 0.12 ± 0.16 (0.86) | 763 ± 95 (1168) | 19 ± 1 (7) |

Compound A - 4-[3,5-bis(1,1-dimethylethyl)-4-hydroxyphenyl]-1(or 3)H-1,2,3-triazole-5-carboxamide
Compound B - 4-[3,5-bis(1,1-dimethylethyl)-4-hydroxyphenyl]-1(or 3)H-1,2,3-triazole-5-methyl ester The acute toxicity of Compound A was determined. Compound A was orally administered in dosages of 10, 30, 300 and 1000 mg/kg to mice by the p.o route and 300 mg/kg by the i.p route. After 1 day, no deaths occurred.

The compounds of formula I, its tautomers described above, salts of the compounds of formula I wherein $R^3$ is OH and tautomers thereof described above can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions, however, the administration can also be effected rectally, for example, in the form of suppositories, or parenterally, for example, in the form of solutions for injection.

The dosage can vary within wide limits and will, of course, be adjusted to the individual requirements in each particular case. The compounds of formula I can be administered at a daily dosage of about 1 mg/kg body weight to about 30 mg/kg body weight.

For the preparation of pharmaceutical dosage forms, the compounds of formula I and their pharmaceutically acceptable addition salts can be processed with pharmaceutically inert inorganic or organic carriers. Lactose, maize starch or related materials, talc, stearic acid or its salts and the like can be used, for example, as carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance, no carriers, however, are required in the case of soft gelatin capsules. Suitable carriers for the preparation of solutions and syrups are, for example, water, polyols, saccharose, invert sugar, glucose and the like. Suitable carriers for injection solutions are, for example, water, alcohols, polyols, glycerol, vegetable oils and the like. Suitable carriers for suppositories are, for example, natural or hardened oils, waxes, fats, semi-liquid or liquid polyols and the like.

The pharmaceutical preparations can also contain preserving agents, solubilizers, stabilizing agents, wetting agents, emulsifying agents, sweetening agents, coloring agents, flavoring agents, salts for varying the osmotic pressure, buffers, coating agents or antioxidants. In addition, they can also contain other therapeutically valuable substances.

The examples which follow further illustrate the invention. All temperatures are given in degree Celsius, unless otherwise stated.

EXAMPLE 1 a. Phenylsulfonylacetamide

A 1-L 3-neck round bottom flask, equipped with mechanical stirrer and thermometer, was charged with 93.52 g (1 mol) of chloroacetamide and 220 mL of dimethylsulfoxide. The charged flask was immersed in an oil bath at 120° C., thereby stirring of the chloroacetamide and dimethylsulfoxide and increasing of the temperature of the same. As soon as a solution was obtained (at about 75° C.), 164.16 g (1 mol) of benzenesulfinic acid sodium salt was added in portions. Heating was continued and a resulting suspension was stirred for 3 hours at an internal temperature between 115°–120° C. The hot suspension was poured into a vigorously stirred 5-L 3-neck flask containing 2 kg of an ice-water mixture. An additional 0.5 L of water was used to rinse the 1-L 3-neck round bottom flask. The additional water was added to the 5-L 3-neck flask. The content of the 5-L 3-neck flask was stirred for an additional 30 minutes. The 5-L 3-neck flask containing a white suspension was then stored in an ice bath overnight. The white suspension was briefly agitated, then filtered through a 2-L sintered-glass funnel. A resulting filter cake was washed in portions with 0.5 L of chilled water, about half of this chilled water volume being required to aid in the transfer of the solids from the 5-L flask to the filter funnel, the remaining portion being applied to the filter funnel directly. The filter cake was dried at 60° C. over potassium hydroxide flakes at 27 torr for 48 hours furnishing 163 g (81.8% yield) of crude phenylsulfonylacetamide. The entire quantity of crude phenylsulfonylacetamide was transferred to a 2-L 3-neck flask equipped with a mechanical stirrer and thermometer. The crude phenylsulfonylacetamide was dissolved in 0.5 L of boiling acetonitrile to give a clear, very light-tan solution. To the resulting solution was added 0.5 L of toluene, followed by 0.5 L of hexane. A resulting white suspension was stirred for 10 minutes at ambient temperature. The 2-L 3-neck flask containing the white suspension was then immersed in an ice bath until the temperature of the white suspension reached 5° C. The white suspension was then filtered through a 600 mL sintered-glass funnel. The resulting filter cake was washed with 100 mL of toluene, followed by 250 mL of hexane. Drying of the filter cake at 75°–80° C. at 30 torr for 20 hours furnished 156.3 g of pure phenylsulfonylacetamide (78.3% yield), mp 157°–158° C.

b. Crude
3-[3,5-Bis(1,1-dimethylethyl)-4-hydroxyphenyl]-2-(phenylsulfonyl)-2-propenamide A 5-liter round-bottom flask, equipped with a thermometer, Dean-Stark water separator and reflux condenser, was charged with a mixture of 250 g (1.027 mol) of 3,5-di-t-butyl-4-hydroxybenzaldehyde hemihydrate (MCI, Lot GA02), 200 g (1 mol) of phenylsulfonylacetamide obtained in Example 1, 300 mL of N,N-dimethylformamide, and 1.2 L of toluene. The mixture was heated in a 5-liter round-bottom flask. Most ingredients dissolved as the flask content reached 90° C. 16 mL of 1-methylpiperazine was then added while heating and stirring was continued until all ingredients were dissolved into a reaction solution. The Dean Stark water separator was filled with cyclohexane. 200 mL of cyclohexane was added into the reaction solution through the condenser. Heating and stirring was continued until reflux commenced. At that time an additional 200 mL of cyclohexane was added to the reaction solution by the same route. Stirring and heating to maintain gentle reflux was continued for 36 hours (internal temperature of reaction solution about 95° C.). At that time heating was discontinued and the hot reaction mixture was diluted, under vigorous stirring, with 500 mL of hexane. A resulting suspension was stirred in an ice bath until an internal temperature of 5° C. was reached, and was filtered by suction using a sintered-glass funnel. The resulting filter cake was washed with 500 mL of a 3:2 mixture of toluene-hexane in 5 portions of 100 mL each. A resulting egg-shell colored material was washed with 200 mL of petroleum ether. Most interstitial liquids were then removed by suction. The filter cake was dried at 60° C. for 48 hours at 30 torr to afford 312 g of crude product.

C. Recrystallization of
3-[3.5-bis(1.1-dimethylethy)-4-hydroxyphenyl]2-phenylsulfonyl)-2-propenamide 312 g of crude 3-[3,5-bis(1,1-dimethylethyl)-4-hydroxyphenyl]-2-(phenylsulfonyl)-2-propenamide obtained as described above was dissolved in 1.2 L of boiling tetrahydrofuran to give a clear solution. The solution was diluted with 1.5 L of toluene. A resulting mixture was concentrated on a rotary evaporator until about 1.1 L of solvent was distilled off. A resulting yellow suspension was filtered at room temperature. A resulting filter cake was washed with 500 mL of a 3:2 mixture of toluene-hexane, followed by 200 mL of petroleum ether. A resulting crystalline product was dried at 60° C. and 25 torr for 24 hours to give 273 g of a cream colored product. This material contained usually between 1.5 and 3.5% of phenylsulfonylacetamide. Mother liquor and wash liquids were concentrated to a volume of 200 mL to afford a crystalline suspension. Filtration, followed by washing of the filter cake with 40 mL of toluene, applied in two equal portions, and 20 mL of petroleum ether gave, after drying 60° C. and 25 torr for 24 hours, 12 g of very crude 3-[3,5-bis(1,1-dimethylethyl)-4-hydroxyphenyl]-2-(phenylsulfonyl)-2-propenamide. This material was added to the 273 g of cream colored product, 3-[3,5-bis(1,1-dimethylethyl)-4-hydroxyphenyl]-2-(phenylsulfonyl)-2-propenamide, previously obtained in this step.

d. Second recrystallization of
3-[3,5-bis(1,1-dimethylethyl)-4-hydroxyphenyl]-2-(phenylsulfonyl)-2-propenamide 285 g of 3-[3,5-bis(1,1-dimethylethyl)-4-hydroxyphenyl]- 2-pentylsulfonyl)-2-propenamide obtained as described above was dissolved in 1.2 L of boiling tetrahydrofuran to give a clear solution. The heat source was removed, the solution was stirred mechanically, then diluted with 2 L of water. A resulting mixture was cooled under stirring stirring until an internal temperature of 5° C. was reached. The resulting cream-colored suspension was filtered, and the collected solid was washed with 500 mL of water and dried at 70° C. and 27 torr for 2 days to constant weight to give a cream-colored powder, 256 g, 61.6% yield, 99.7% pure (HPLC).

e. Crude
4-[3.5-bis(1.1-dimethylethyl)-4-hydroxyphenyl]-(or3)H-1,2,3-triazole-5-carboxamide A yellow suspension of 235 g of 3-[3,5-bis(1,1-dimethylethyl)-4-hydroxyphenyl]-2-(phenylsulfonyl)-2-propenamide (0.566 mol) obtained as described above and 44 g of sodium azide (0.677 mol) in 540 mL of 2-methoxyethanol (ethylene glycol monomethyl ether) was stirred mechanically in a 3-L 3-neck flask, equipped with an air condenser and a thermometer. The yellow suspension was stirred and heated in a mantle at 100° C. for 3 hours. During this time the yellow suspension changed to a brown and, finally, to a dark olive-colored solution. After the three hour heating period 1.3 L of water was added to the dark olive-colored solution, the heating mantle was replaced with an ice bath and stirring was continued until the internal temperature reached 5° C. A resulting suspension was filtered. A resulting filter cake was washed with 750 mL of water. The washed filter cake was dried overnight at 70° C. over potassium hydroxide flakes at 30 torr to constant weight, to afford a main lot of 161 g (89.9% yield) of crude 4-[3,5-bis(1,1-dimethylethyl)- 4- hydroxyphenyl]-1 (or3)H-1,2,3-triazole-5-carboxamide. The mother liquor and aqueous washings were combined and extracted a total of-four times with a total of 3 L of methyl ketone. The first and second extracts were combined and washed with 100 mL of water followed by 50 mL of brine. A resulting solution was dried over 20 g of magnesium sulfate, filtered and evaporated to give 13 g of crude 4-[3,5-bis(1,1-dimethylethyl)- 4-hydroxyphenyl]-1 (or 3)H-1,2,3-triazole-5-carboxamide. A similar treatment of the third and fourth extracts gave an additional 4 g of 4-[3,5-bis(1,1-dimethylethyl)-4-hydroxyphenyl]-1 (or 3)H-1,2,3-triazole-5-carboxamide.

f. First recrystalization of 4-[3,5-bis(1,1-dimethylethy)-4-hydroxyphenyl]-1(or 3)H-1,2,3-triazole-5-carboxamide The materials recovered by extraction were combined with the main lot of crude 4-[3,5-bis(1,1-dimethylethyl)-4-hydroxyphenyl]-1(or3)H, 1,2,3-triazole-5-carboxamide and dissolved in 700 mL of boiling tetrahydrofuran. A resulting solution was diluted with 1 L of toluene and concentrated on the rotary evaporator until about 1.1 L of solvent was distilled off. A resulting suspension of cream colored crystals was refrigerated overnight, then filtered. A resulting filter cake was washed with 350 mL of a 3:2 mixture of toluene-hexane to remove a brown mother liquor. Resulting solids were washed with 150 mL of petroleum ether and dried at 70° C. and 27 torr to constant weight to give 156 g of a cream-colored, crystalline powder.

g. Second recrystallization of 4-[3.5-bis(1,1-dimethylethyl)-4-hydroxyphenyl]1-1 (or3)H-1,2,3-triazole-5-carboxamide The entire material obtained in the previous step was dissolved in 1 L of boiling acetone. A resulting solution was allowed to cool to room temperature and was passed through a plug of flash-chromatography grade silica gel (Universal Adsorbents Inc. Lot No. UA205, particle size -32-64). This filtration step was conducted by charging a sintered-glass funnel of 8.5 cm diameter and medium porosity to give a bed height of 5 cm and equilibrating the silica gel with acetone. A resulting filtrate was collected in a filter flask under slightly reduced pressure. The plug of silica gel was washed with 600 mL of acetone. The wash liquids were combined with the original filtrate and a resulting clear and nearly colorless solution was concentrated on the rotary evaporator to a volume of about 800 mL. This solution was diluted with 500 mL of toluene and the solution was concentrated to remove most of the acetone. A resulting suspension was further diluted with 250 mL of toluene and concentrated to a volume of about 700 mL. A suspension thus obtained was refrigerated overnight and filtered, and a collected solid was washed with 250 mL of toluene and concentrated to a volume of about 700 mL. A resulting suspension was refrigerated overnight and filtered, and the collected solid was washed with 250 mL of a 3:2 mixture of toluene-hexane and then with 200 mL of petroleum ether. The resulting material was dried at 70° C. and 27 torr to constant weight to give 147 g of a white, crystalline powder.

h. Third recrystallization of 4-[3,5-bis(1,1-dimethylethyl)-4-hydroxyphenyl]-1-(or3)H-1,2,3-triazole-5-carboxamide A total of 387 g of pooled materials prepared by the protocol outlined above was dissolved in 4 L of boiling acetone. To a resulting clear and nearly colorless solution was added 4 L of water according to the following schedule. 1.4 L was added at once and the resulting solution was concentrated on the rotary evaporator until a thick crystalline suspension was obtained. The white suspension was then diluted with the remaining 2.6 L of water. A resulting mixture was shaken vigorously and was filtered. A resulting filter cake was washed with 600 mL of water and dried at 65° C. at 30 torr for 18 hours under a slight air-bleed, then for 2 days over potassium hydroxide flakes at 70° C. at 30 torr (no residual acetone or toluene was detectable by NM spectroscopy at this stage), and finally at 84° C. and 30 torr under a slight air-bleed for 2 days to give 367 of 100% pure (HPLC) 4-[3,5-bis(1,1-dimethylethyl)-4-hydroxyphenyl]-1(or 3)H-1,2,3-triazole-5-carboxamide.

EXAMPLE A

Tablets of the following compositions are prepared as described below:

| TABLET FORMULATION (Wet Granulation) | | | | | |
|---|---|---|---|---|---|
| Item | Ingredients | | mg/tablet | | |
| 1 | Compound A | 25 | 100 | 250 | 500 |
| 2 | Anhydrous Lactose | 83 | 35 | 19 | 38 |
| 3 | Croscarmellose Sodium | 6 | 8 | 16 | 32 |
| 4 | Povidone K30 | 5 | 6 | 12 | 24 |
| 5 | Magnesium Stearate | 1 | 1 | 3 | 6 |
| | Total Weight | 120 | 150 | 300 | 600 |

Compound A is 4-[3,5-bis(1,1-dimethylethyl)-4-hydroxyphenyl]-1(or 3)H-1,2,3-triazole-5-carboxamide Manufacturing Procedure:
1. Mix Items 1, 2 and 3 in a suitable mixer for 15 minutes.
2. Granulate the powder mix from Step 1 with 20% polyvinyl pyrolidone K30 Solution.
3. Dry the granulation from Step 2 at 50° C.
4. Pass the granulation from Step 3 through a suitable milling equipment.
5. Add the Item 5 to the milled granulation from Step 4 and mix for 3 minutes.
6. Compress the granulation from Step 5 on a suitable press.

EXAMPLE B

Capsules of the following compositions are prepared as described below:

| CAPSULE FORMULATION | | | | | |
|---|---|---|---|---|---|
| Item | Ingredients | | mg/tablet | | |
| 1 | Compound A | 25 | 100 | 250 | 500 |
| 2 | Hydrous Lactose | 123 | 148 | — | — |
| 3 | Corn Starch | 35 | 40 | 35 | 70 |
| 4 | Talc | 15 | 10 | 12 | 24 |
| 5 | Magnesium Stearate | 2 | 2 | 3 | 6 |
| | Total Weight | 200 | 300 | 300 | 600 |

Manufacturing Procedure:
1. Mix Items 1, 2 and 3 in a suitable mixer for 30 minutes.
2. Add Items 4 and 5 and mix for 3 minutes.
3. Fill into a suitable capsule.

I claim:
1. A compound of the formula

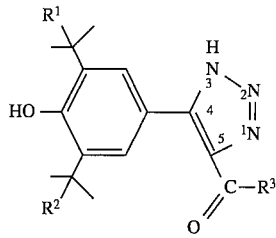

wherein $R^1$ and $R^2$ are independently lower alkyl;

$R^3$ is —$NR^4R^5$ or —$OR^6$;

$R^4$ is hydrogen, hydroxy, lower alkyl, lower alkenyl, lower alkoxy, cyclopropyl, fluoro substituted lower alkyl, chloro substituted lower alkyl, hydroxy substituted lower alkyl, alkoxy substituted lower alkyl, or amino substituted lower alkyl;

$R^5$ is hydrogen, hydroxy, alkyl, alkenyl, alkoxy, cycloalkyl, fluoro substituted alkyl, chloro substituted alkyl, hydroxy substituted alkyl, alkoxy substituted alkyl, amino substituted alkyl, phenyl, phenoxy, phenyl substituted alkyl, phenyl substituted alkenyl, phenoxy substituted alkyl, phenylcarbonyl, alkylcarbonyl, or a 5 or 6 membered heterocyclic group;

when $R^4$ is hydroxy or lower alkoxy, $R^5$ is not hydroxy, alkoxy or phenoxy; and $R^6$ is hydrogen, alkyl, phenyl, or phenyl substituted alkyl;

its tautomer wherein the hydrogen of the triazole ring occupies position 1 of the triazole ring, and a pharmaceutically acceptable salt of the compound of formula I wherein $R^3$ is —OH or its tautomer wherein the hydrogen of the triazole ring occupies position 1 of the triazole ring.

2. A compound according to claim 1, wherein $R_1$ and $R_2$ each is methyl.

3. A compound according to claim 1, wherein $R^3$ is —$NR^4R^5$.

4. A compound according to claim 3, wherein $R^4$ is hydrogen, methyl, methoxy, ethyl, or ethoxy.

5. A compound according to claim 3, wherein $R^5$ is hydrogen, hydroxy, $C_1$–$C_7$ alkyl, $C_2$–$C_7$ alkenyl, $C_1$–$C_7$ alkoxy, cyclopropyl, fluorosubstituted $C_1$–$C_7$ alkyl or hydroxysubstituted $C_1$–$C_7$ alkyl.

6. A compound according to claim 1, selected from the group consisting of:

4-[3,5-bis(1,1-dimethylethyl)-4-hydroxyphenyl]-1(or3)H- 1,2,3-triazole-5-carboxamide;

4-[3,5-bis(1,1-dimethylethyl)-4-hydroxyphenyl]-N-methyl-1(or3)H- 1,2,3-triazole-5-carboxamide;

4-[3,5-bis(1,1-dimethylethyl)-4-hydroxyphenyl]-N-ethyl-1(or3)H- 1,2,3-triazole-5-carboxamide;

4-[3,5-bis(1,1-dimethylethyl)-4-hydroxyphenyl]-N-methoxy-1(or3)H- 1,2,3-triazole-5-carboxamide;

4-[3,5-bis(1,1-dimethylethyl)-4-hydroxyphenyl]-N-hydroxy-N-methyl-1(or3 )H-1,2,3-triazole-5-carboxamide;

4-[3,5-bis(1,1-dimethylethyl)-4-hydroxyphenyl]-N-cyclopropyl-1(or3)H- 1,2,3-triazole-5-carboxamide;

4-[3,5-bis(1,1-dimethylethyl)-4-hydroxyphenyl]-N-(2,2,2-trifluoroethyl)-1(or3)H-1,2,3-triazole-5-carboxamide;

4-[3,5-bis(1,1-dimethylethyl)-4-hydroxyphenyl]-N-(2-fluoroethyl)-1(or3)H- 1,2,3-triazole-5-carboxamide; and 4-[3,5-bis(1,1-dimethylethyl)-4-hydroxyphenyl]-N-(2-hydroxyethyl)- 1(or3)H-1,2,3triazole-5-carboxamide.

7. A compound according to claim 6, 4-[3,5-bis(1,1-dimethylethyl)-4-hydroxyphenyl]-1(or3)H- 1,2,3-triazole-5-carboxamide.

8. A pharmaceutical composition comprising an effective amount of a compound of the formula

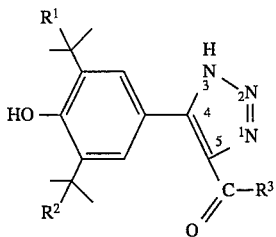

wherein $R^1$ and $R^2$ are independently lower alkyl;

$R^3$ is —$NR^4R^5$ or —$OR^6$;

$R^4$ is hydrogen, hydroxy, lower alkyl, lower alkenyl, lower alkoxy, cyclopropyl, fluoro substituted lower alkyl, chloro substituted lower alkyl, hydroxy substituted lower alkyl, alkoxy substituted lower alkyl, or amino substituted lower alkyl;

$R^5$ is hydrogen, hydroxy, alkyl, alkenyl, alkoxy, cycloalkyl, fluoro substituted alkyl, chloro substituted alkyl, hydroxy substituted alkyl, alkoxy substituted alkyl, amino substituted alkyl, phenyl, phenoxy, phenyl substituted alkyl, phenyl substituted alkenyl, phenoxy substituted alkyl, phenylcarbonyl, alkylcarbonyl, or a 5 or 6 membered heterocyclic group;

when $R^4$ is hydroxy or lower alkoxy, $R^5$ is not hydroxy, alkoxy, or phenoxy;

$R^6$ is hydrogen, alkyl, phenyl, or amino substituted phenyl;

its tautomer wherein the hydrogen of the triazole ring occupies position 1 of the triazole ring, or a pharmaceutically acceptable salt of the compound of formula I wherein $R^3$ is —OH or its tautomer wherein the hydrogen of the triazole ring occupies position 1 of the triazole ring;

and an inert carrier.

9. A pharmaceutical composition of claim 8, wherein a compound of formula I is selected from the group consisting of:

4-[3,5-bis(1,1-dimethylethyl)-4-hydroxyphenyl]-1(or3)H-1,2,3-triazole-5-carboxamide;

4-[3,5-bis(1,1-dimethylethyl)-4-hydroxyphenyl]-N-methyl-1(or3)H-1,2,3-triazole-5-carboxamide;

4-[3,5-bis(1,1-dimethylethyl)-4-hydroxyphenyl]-N-ethyl-1(or3)H-1,2,3-triazole-5-carboxamide;

4-[3,5-bis(1,1-dimethylethyl)-4-hydroxyphenyl]-N-methoxy-1(or3)H- 1,2,3-triazole-5-carboxamide;

4-[3,5-bis(1,1-dimethylethyl)-4-hydroxyphenyl]-N-hydroxy-N-methyl-1(or3)H-1,2,3-triazole-5-carboxamide;

4-[3,5-bis(1,1-dimethylethyl)-4-hydroxyphenyl]-N-cyclopropyl-1(or 3)H-1,2,3-triazole-5-carboxamide;

4-[3,5-bis(1,1-dimethylethyl)-4-hydroxyphenyl]-N-(2,2,2-trifluoroethyl)- 1(or3)H-1,2,3-traizole-5-carboxamide;

4-[3,5-bis(1,1-dimethylethyl)-4-hydroxyphenyl]-N-(2-fluoroethyl)-1(or3)H-1,2,3-triazole-5-carboxamide; and 4-[3,5-bis(1,1-dimethylethyl)-4-hydroxyphenyl]-N-(2-hydroxyethyl)- 1(or3)H-1,2,3-triazole-5-carboxamide.

10. A pharmaceutical composition according to claim 9, wherein the compound of formula I is 4-[3,5-bis(1,1-dimethylethyl)-4-hydroxyphenyl]-1(or3)H- 1,2,3-triazole-5-carboxamide.

11. A method of treating inflammation which comprises administering to a host requiring such treatment an effective amount of a compound of the formula

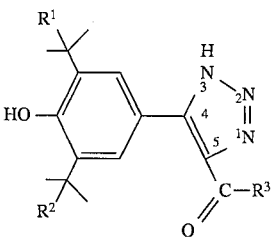

wherein

R$^1$ and R$^2$ are independently lower alkyl;

R$^3$ is —NR$^4$R$^5$ or —OR$^6$;

R$^4$ is hydrogen, hydroxy, lower alkyl, lower alkenyl, lower alkoxy, cyclopropyl, fluoro substituted lower alkyl, chloro substituted lower alkyl, hydroxy substituted lower alkyl, alkoxy substituted lower alkyl, or amino substituted lower alkyl;

R$^5$ is hydrogen, hydroxy, alkyl, alkenyl, alkoxy, cycloalkyl, fluoro substituted alkyl, chloro substituted alkyl, hydroxy substituted alkyl, alkoxy substituted alkyl, amino substituted alkyl, phenyl, phenoxy, phenyl substituted alkyl, phenyl substituted alkenyl, phenoxy substituted alkyl, phenylcarbonyl, alkylcarbonyl, or a 5 or 6 membered heterocyclic group; when R$^4$ is hydroxy or lower alkoxy, R$^5$ is not hydroxy, alkoxy or phenoxy; and R$^6$ is hydrogen, alkyl, phenyl, or phenyl substituted alkyl; its tautomer wherein the hydrogen of the triazole ring occupies position 1 of the triazole ring, or a pharmaceutically acceptable salt of the compound of formula I wherein R$^3$ is —OH or its tautomer wherein the hydrogen of the triazole ring occupies position 1 of the triazole ring.

12. A method of claim 10, wherein a compound of formula (I) is selected from the group consisting of:

4-[3,5-bis(1,1-dimethylethyl)-4-hydroxyphenyl]-1(or3)H-1,2,3-triazole-5-carboxamide;

4-[3,5-bis(1,1-dimethylethyl)-4-hydroxyphenyl]-N-methyl-1(or3)H-1,2,3-triazole-5-carboxamide;

4-[3,5-bis(1,1-dimethylethyl)-4-hydroxyphenyl]-N-ethyl-1(or3)H-1,2,3-triazole-5-carboxamide;

4-[3,5-bis(1,1-dimethylethyl)-4-hydroxyphenyl]-N-methoxy-1(or3)H-1,2,3-triazole-5-carboxamide;

4-[3,5-bis(1,1-dimethylethyl)-4-hydroxyphenyl]-N-hydroxy-N-methyl-1(or3)H-1,2,3-triazole-5-carboxamide;

4-[3,5-bis(1,1-dimethylethyl)-4-hydroxyphenyl]-N-cyclopropyl-1(or3)H-1,2,3-triazole-5-carboxamide;

4-[3,5-bis(1,1-dimethylethyl)-4-hydroxyphenyl]-N-(2,2,2-trifluoroethyl)-1(or3)H-1,2,3-triazole-5-carboxamide;

4-[3,5-bis(1,1-dimethylethyl)-4-hydroxyphenyl]-N-(2-fluoroethyl)-1(or3)H-1,2,3-triazole-5-carboxamide; and 4-[3,5-bis(1,1-dimethylethyl)-4-hydroxyphenyl]-N-(2-hydroxyethyl)-1(or3)H-1,2,3-triazole-5-carboxamide.

13. A method of claim 12, wherein the compound of formula (I) is 4-[3,5-bis(1,1-dimethylethyl)-4-hydroxyphenyl]-1(or3)H-1,2,3-triazole-5-carboxamide.

14. A compound of the formula

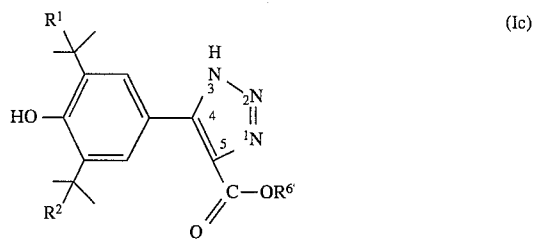

wherein

R$^1$ and R$^2$ are independently lower alkyl, and

R$^{6'}$ is alkyl, phenyl or phenyl substitued alkyl, and a tautomer thereof wherein the hydrogen of the triazole ring occupies position 1 of the triazole ring.

15. A compound of the formula

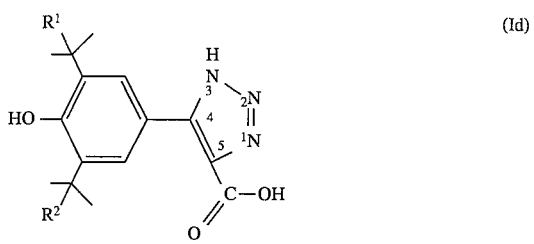

and a tautomer thereof wherein the hydrogen of the triazole ring occupies position 1 of the triazole ring.

* * * * *

UNITED STATES PATENT AND TRADEMARK OFFICE
CERTIFICATE OF CORRECTION

PATENT NO. : 5,523,310
DATED : June 4, 1996
INVENTOR(S) : Hubert Maehr

It is certified that error appears in the above-indentified patent and that said Letters Patent is hereby corrected as shown below:

IN THE CLAIMS

- Claim 14, Column 20, line 31: "substitued" should read
    --- substituted --- .

Signed and Sealed this

Seventeenth Day of September, 1996

*Attest:*

BRUCE LEHMAN

*Attesting Officer*        *Commissioner of Patents and Trademarks*